(12) United States Patent  
Forsell

(10) Patent No.: US 12,115,092 B2  
(45) Date of Patent: Oct. 15, 2024

(54) REFLUX TREATMENT DEVICE

(71) Applicant: Peter Mats Forsell, Obwalden (CH)

(72) Inventor: Peter Mats Forsell, Obwalden (CH)

( * ) Notice: Subject to any disclaimer, the term of this patent is extended or adjusted under 35 U.S.C. 154(b) by 0 days.

(21) Appl. No.: 18/610,706

(22) Filed: Mar. 20, 2024

(65) Prior Publication Data

US 2024/0225875 A1 Jul. 11, 2024

Related U.S. Application Data

(63) Continuation of application No. 18/111,913, filed on Feb. 21, 2023, which is a continuation of application No. 16/636,344, filed as application No. PCT/EP2018/072042 on Aug. 14, 2018, now Pat. No. 11,596,539.

(51) Int. Cl.
```
A61F 5/00      (2006.01)
A61B 17/00     (2006.01)
A61B 17/04     (2006.01)
A61B 17/34     (2006.01)
```

(52) U.S. Cl.
CPC ...... *A61F 5/0089* (2013.01); *A61B 17/00234* (2013.01); *A61B 17/0469* (2013.01); *A61B 17/3468* (2013.01); *A61F 5/0069* (2013.01); *A61B 2017/00296* (2013.01); *A61B 2017/003* (2013.01); *A61B 2017/00389* (2013.01); *A61B 2017/0042* (2013.01); *A61B 2017/00827* (2013.01)

(58) Field of Classification Search
CPC ................ A61F 5/0089; A61F 5/0069; A61B 17/00234; A61B 17/0469; A61B 17/3468; A61B 2017/00296; A61B 2017/003; A61B 2017/00389; A61B 2017/0042; A61B 2017/00827

See application file for complete search history.

(56) References Cited

U.S. PATENT DOCUMENTS

| | | | | |
|---|---|---|---|---|
| 4,412,530 | A * | 11/1983 | Burton | A61F 2/004 128/DIG. 25 |
| 4,773,393 | A * | 9/1988 | Haber | A61F 2/004 128/DIG. 25 |
| 4,832,680 | A * | 5/1989 | Haber | A61F 2/004 623/4.1 |
| 6,098,629 | A * | 8/2000 | Johnson | A61B 17/12022 128/897 |
| 6,238,335 | B1 * | 5/2001 | Silverman | A61B 17/1204 600/29 |
| 6,540,789 | B1 * | 4/2003 | Silverman | A61B 17/12186 607/40 |
| 10,420,665 | B2 * | 9/2019 | Sharma | A61B 6/12 |
| 10,449,076 | B2 * | 10/2019 | Peter | A61F 5/003 |
| 10,905,580 | B2 * | 2/2021 | Forsell | A61F 5/0063 |
| 11,471,026 | B2 * | 10/2022 | Piskun | A61B 1/00082 |

(Continued)

FOREIGN PATENT DOCUMENTS

EP 1004330 A1 * 5/2000 ......... A61N 1/36007

*Primary Examiner* — Suzette J Gherbi

(57) ABSTRACT

A movement restriction device for use in a surgical procedure for treating reflux disease in a patient. The movement restriction device being adapted to restrict movement of the cardia sphincter and to contact the fundus of the patient's stomach. The movement restriction device has a body having a substantially spherical shape comprising a plurality of facets.

16 Claims, 10 Drawing Sheets

(56) References Cited

U.S. PATENT DOCUMENTS

| | | | |
|---|---|---|---|
| 2010/0161075 A1* | 6/2010 | Silverman | A61B 17/12099 623/23.65 |
| 2011/0009801 A1* | 1/2011 | Blaeser | A61F 2/04 604/8 |
| 2023/0190464 A1* | 6/2023 | Murad | A61M 25/10 623/2.11 |

* cited by examiner

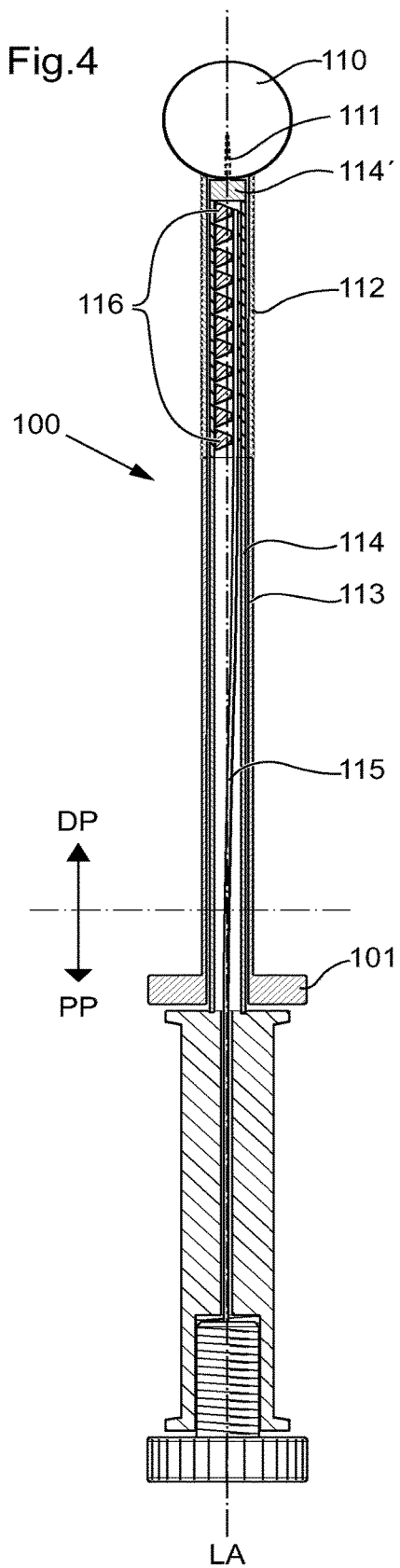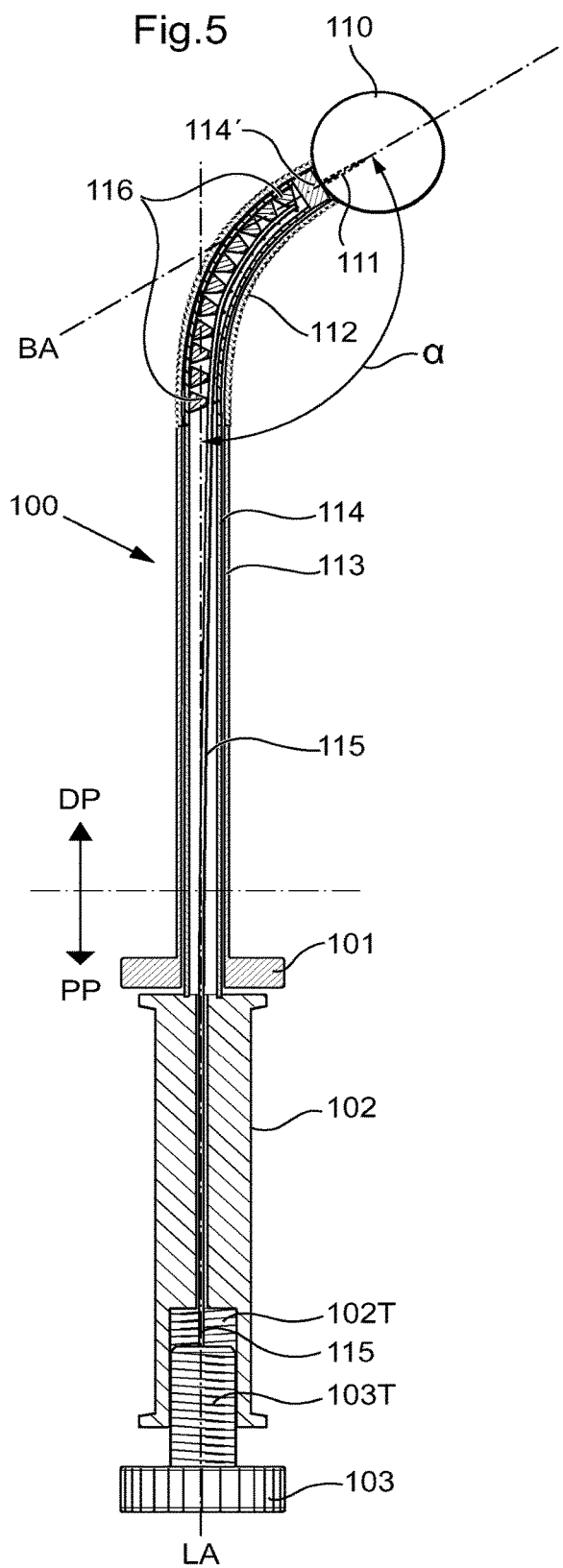

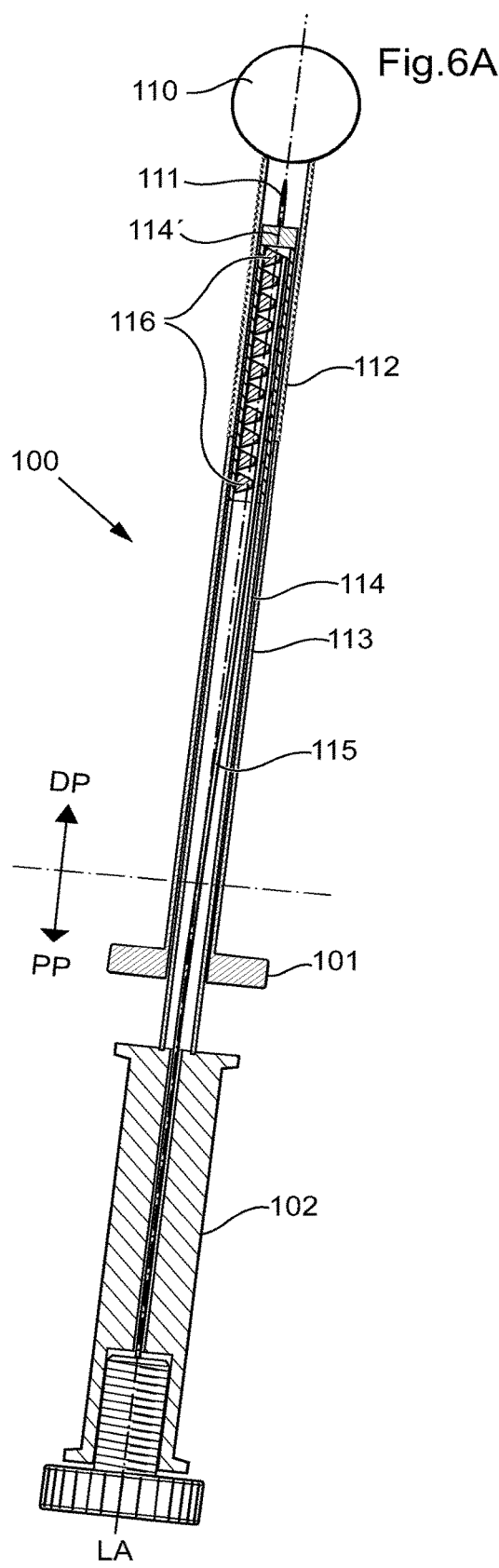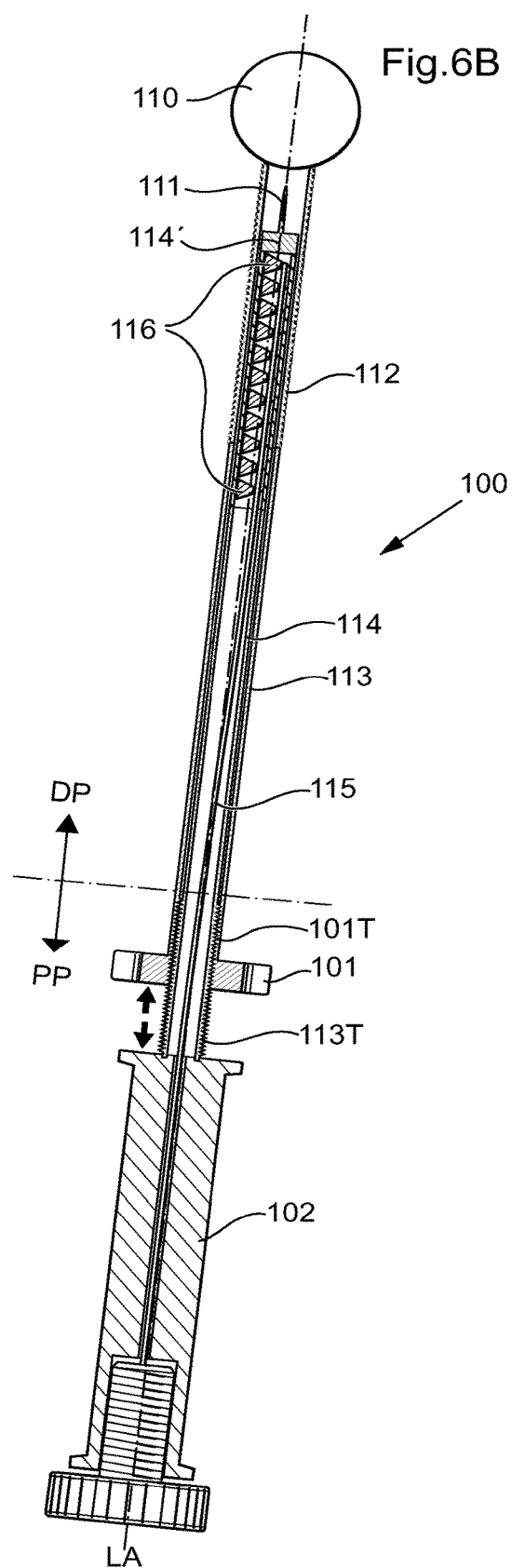

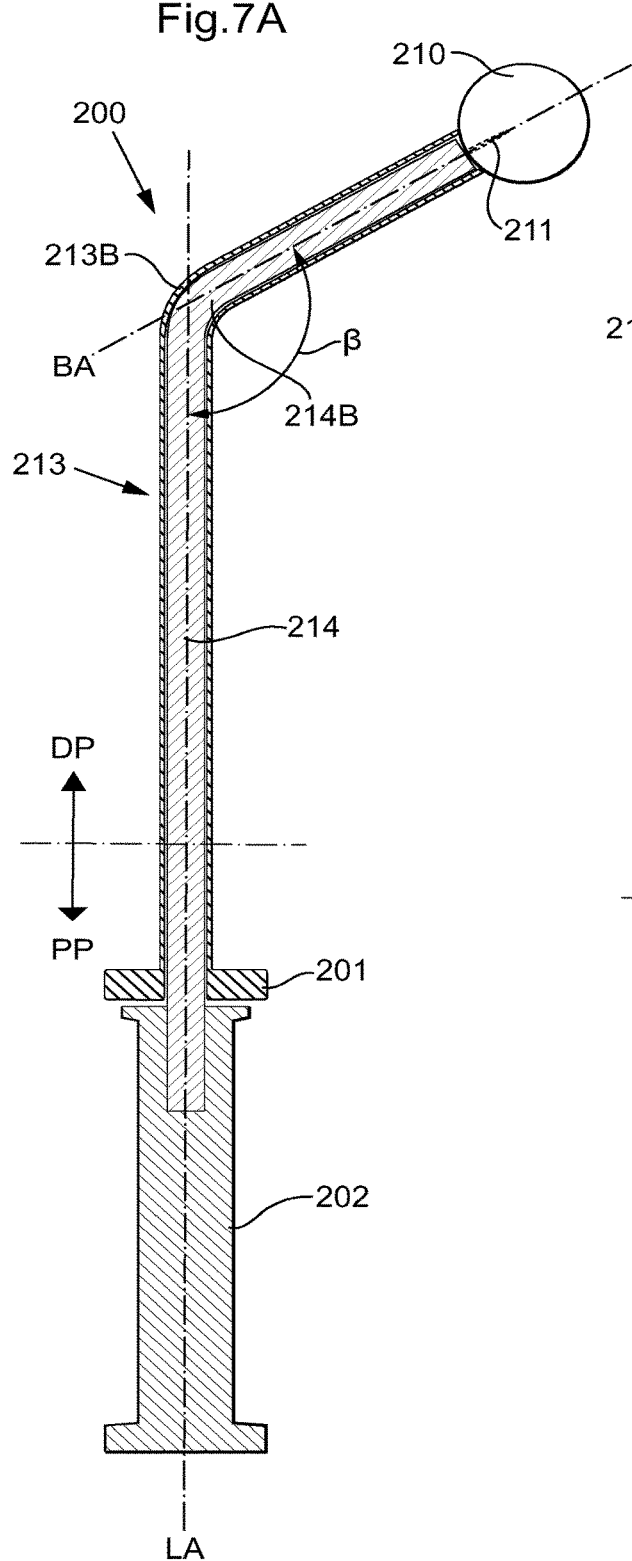
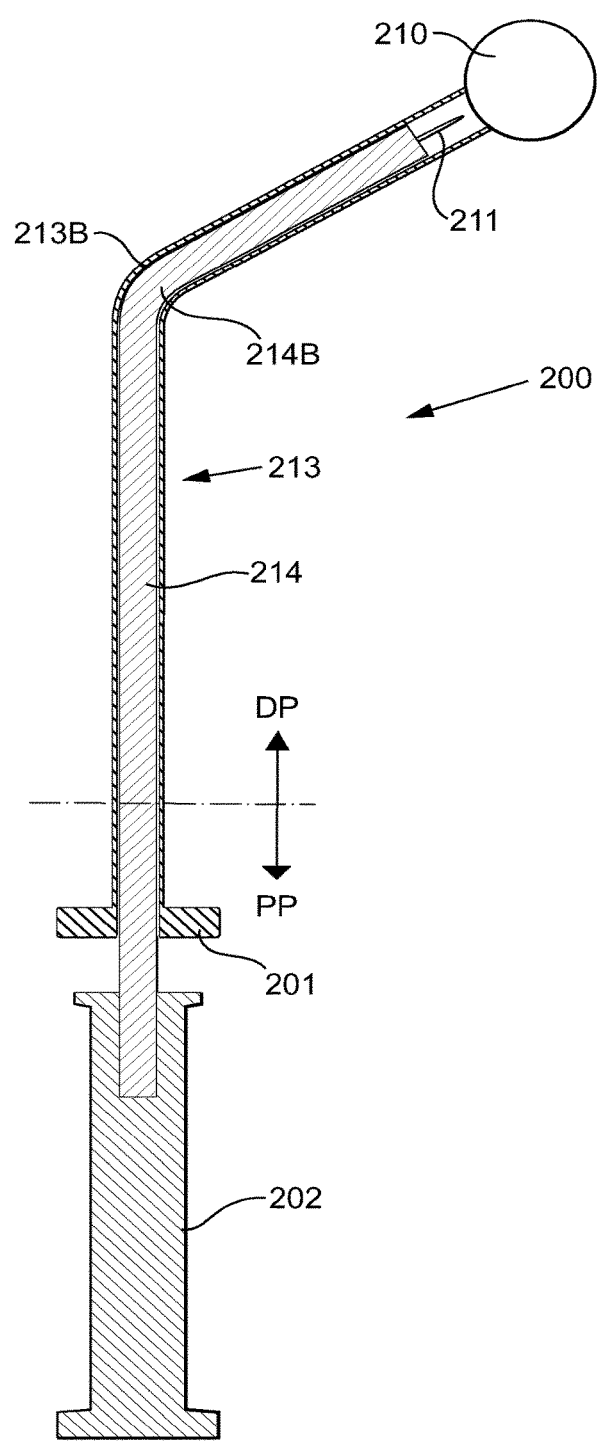

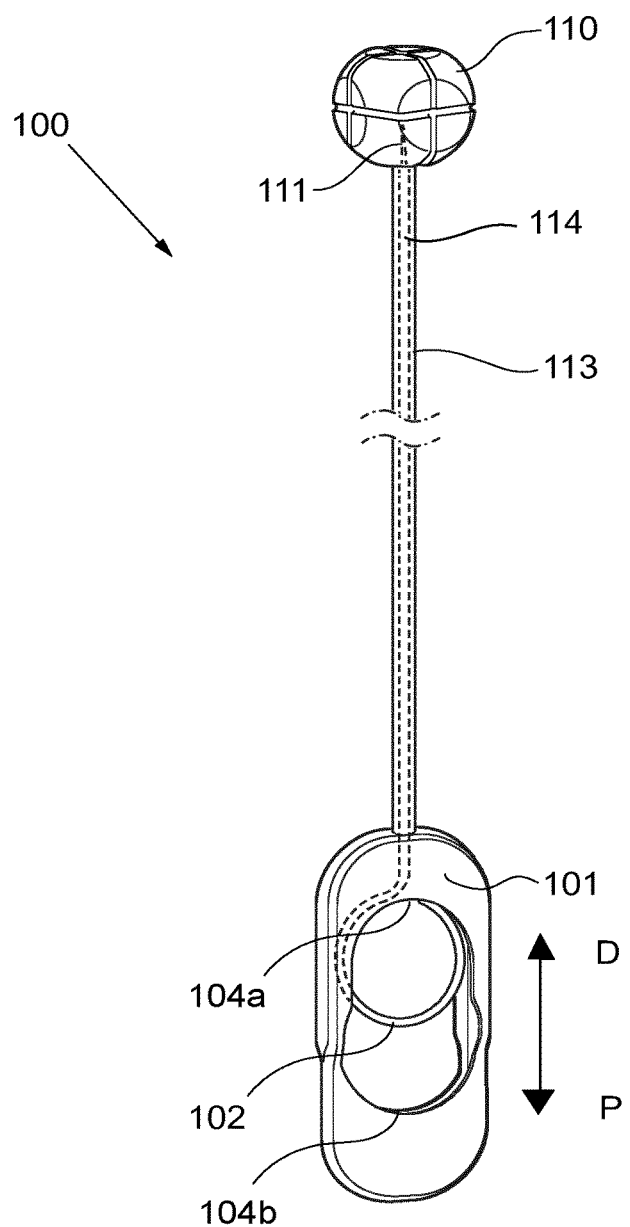

400~~~~~~~~~~~~~~~~~~

REFLUX TREATMENT DEVICE

This application is a Continuation of U.S. patent application Ser. No. 18/111,913, filed Feb. 21, 2023, which is a Continuation of U.S. patent application Ser. No. 16/636,344, filed Feb. 4, 2020 and issued as U.S. Pat. No. 11,596,539 on Mar. 7, 2023, which is the National Stage Entry of PCT/EP2018/072042, which designates the U.S. and is filed Aug. 14, 2018, and claims priority from Swedish Patent Application 1750996-9, filed Aug. 16, 2017, the entire contents of each of which are hereby incorporated by reference in this application.

TECHNICAL FIELD

The present invention relates generally to an instrument for treating Gastro Esophageal Reflux Disease (GERD) and/or Obesity in a human patient.

BACKGROUND

Gastro Esophageal Reflux Disease (GERD), or acid reflux disease, is a chronic condition resulting in mucosal damage in the esophagus produced by the recurring occurrence of acid reflux in the esophagus. This is commonly due to transient or permanent changes in the barrier between the esophagus and the stomach. This can be due to incompetence of the lower esophageal sphincter (LES), transient LED relaxation, impaired expulsion of gastric reflux from the esophagus, or a hiatal hernia.

Gastro Esophageal Reflux Disease can be treated in a number of ways, where surgical treatments are sometimes preferred over longtime medication. A standard surgical treatment is Nissen funduplication where the upper portion of the stomach is wrapped around LES to strengthen the sphincter and prevent acid reflux and to repair hiatal hernia. This procedure often done laparoscopically and is hard to perform transorally.

Another surgical treatment is to create an anti-reflux valve of fundus tissue. This treatment can be performed transorally, by using an endoscope to visualize the Z-line and attract tissue creating a suitable valve which is then fastened. Such treatment is hard and requires a skilled endoscopist. It includes numerous steps in each procedure, typically manipulating tissue more than two times and applying a plurality of individual fasteners to create an anti-reflux valve. Some patients also suffer from hiatal hernia which is an additional step to treat. This both increases time consumption of the endoscopist and each added step increase the risk of mistakes which can potentially be hard to undo.

From experience with implantation of medical devices, it is known that sutures between an implanted device and human tissue will not hold in the long term. For long term implantation of a device, there are two possibilities to keep the device in place. A first solution has been to suture human tissue to human tissue, to thereby keep the device in place. A second approach has been to provide sutures holding a device in place in the short term and to allow in-growth of human tissue into the device for holding the device in place over the long term.

A problem with providing an implantable device associated with the esophagus is that the outer surface of the esophagus is only comprised of esophagus muscle tissue, which is very easy to damage or migrate through. This is probably one reason why the Anglechik prosthesis described above has resulted in many complications, such as migration.

The stomach, on the other hand, has a serosa on its outside, thereby providing a much stronger membrane for suturing. Thus, suturing a device directly to the stomach wall provides a better result than suturing an implanted device to the esophagus.

Today, there exists a need for a long term treatment of GERD that is more effective than prior treatments and which does not result in any severe complications.

Surgical treatments in the upper gastrointestinal tract are today generally complicated to do in a minimal or non-invasive manner. The treatment's level of invasiveness depends on the arrangement of surgical instruments and the handling thereof. Thus, there exists a need for an instrument for performing surgical operations in a more effective way than prior instruments for surgical treatments in the stomach cavity.

SUMMARY OF THE INVENTION

It is an object of the present invention to overcome, or at least reduce, some of the problems associated with existing surgical treatments of Gastro Esophageal Reflux Disease (GERD). It is another object of the present invention to provide an instrument and method for treating Gastro Esophageal Reflux Disease. These objects and others are obtained by appended claims.

A surgical instrument for placement of a movement restriction device for use in a surgical procedure for treating reflux disease in a patient is provided. The surgical instrument comprises a sleeve and a holding device configured to engage the movement restriction device, wherein the holding device is configured to be placed within the sleeve and be displaceable in relation to the sleeve. The instrument further comprises a first handling portion connected to the sleeve, and a second handling portion connected to the holding device. The handling of at least one of the first and second handling portion creates relative displacement of the holding device in relation to the sleeve, which disengages the holding device from the movement restriction device for performing the placement of the movement restriction device. The instrument provides secure holding of the movement restriction device during the surgical procedure as well as easy disengagement upon completion of the surgical procedure. The instrument also reduces the risk that the movement restriction device is removed or displaced from its fixated position when the instrument is retracted.

According to one embodiment, the surgical instrument comprises a distal portion, configured to enter the body of the patient in use, and a proximal portion, configured to remain outside of the body of the patient in use. The holding device is positioned in the distal portion and the first and second handling portions are positioned in the proximal portion.

According to one embodiment, the holding device is positioned on an elongated member connected to the second handling portion.

According to one embodiment, the holding device comprises a protruding member configured to engage a recess of the movement restriction device.

According to one embodiment, the first handling portion is linearly displaceable in relation to the second handling portion along a primary length axis of the instrument, and in an alternative embodiment, the first handling portion is rotationally displaceable in relation to the second handling portion around a primary length axis of the instrument.

The first handling portion may comprise a threaded portion and at least one of the second handling portion and the sleeve comprises a corresponding threaded portion, such that rotational displacement of the first handling portion in relation to the second handling portion creates linear displacement of the first handling portion in relation to the second handling portion, along the primary length axis of the instrument.

According to one embodiment, the distal portion is bent in relation to the primary length axis of the instrument. The distal portion may be bent more than 20° in relation to the primary length axis of the instrument, or more than 30° in relation to the primary length axis of the instrument, or more than 45° in relation to the primary length axis of the instrument, or more than 60° in relation to the primary length axis of the instrument, or more than 75° in relation to the primary length axis of the instrument, or more than 90° in relation to the primary length axis of the instrument. The bend enables the instrument to be placed in the required positioned by rotation of the instrument.

The distal portion of the sleeve may be rigid and a distal portion of the elongated member is flexible, alternatively the distal portion of the sleeve is flexible and a distal portion of the elongated member is rigid.

According to one embodiment, the distal portion is flexible such that the distal portion can be bent in relation to the primary length axis of the instrument. The distal portion may be operably flexible such that the surgeon can bend the distal portion during the surgical procedure, which may mean that the elongated member is operably flexible such that the surgeon can bend the distal portion during the surgical procedure. In one embodiment the operably flexible distal portion is configured to be bent in excess of 30°. In one embodiment the operably flexible distal portion is configured to be bent in excess of 45°. In one embodiment the operably flexible distal portion is configured to be bent in excess of 60°. In one embodiment the operably flexible distal portion is configured to be bent in excess of 75°. In one embodiment the operably flexible distal portion is configured to be bent in excess of 90°.

According to one embodiment, the proximal portion further comprises a third handling portion for operating the operably flexible distal portion during the surgical procedure. The third handling portion may be linearly displaceable in relation to the second handling portion along a primary length axis of the instrument, for operating the operably flexible distal portion during the surgical procedure. In an alternative embodiment, the third handling portion is rotationally displaceable in relation to the second handling portion around a primary length axis of the instrument, for operating the operably flexible distal portion during the surgical procedure.

According to one embodiment, the third handling portion comprises a threaded portion and the second handling portion comprises a corresponding threaded portion, such that rotational displacement of the third handling portion in relation to the second handling portion creates linear displacement of the third handling portion in relation to the second handling portion along the primary length axis of the instrument, for operating the operably flexible distal portion during the surgical procedure.

According to one embodiment, the sleeve comprises a rigid portion and a flexible portion configured to bend, and wherein the sleeve is displaceable relative to the holding device, such that the point on the surgical instrument in which the bending may start can be moved.

The surgical instrument according to any one of the embodiments herein may be configured to be inserted into the abdomen of a patient through a trocar.

According to one embodiment, the first handling portion comprises at least one groove or recess adapted to house at least part of the second handling portion. Preferably, the first handling portion comprises at least two grooves or recesses running along the length axis of the instrument. The grooves or recesses supports the second handling portion during displacement. Preferably, the grooves or recesses prevent or hinders movement in the width axis of the instrument.

According to one embodiment, the at least one groove or recess is adapted to allow relative displacement of the second handling portion and the first handling portion. Preferably, at least part of the second handling portion is positioned in the at least one groove or recess during relative displacement of the first handling portion in relation to the second handling portion.

According to some embodiments, the holding device is integrated with the elongated member connected to the second handling portion. The holding device may be integrally formed in one piece with the elongated member. This can be achieved by providing the elongated member in the form of a wire.

According to some embodiments, the second handling portion is integrated with the elongated member. The second handling portion may be integrally formed in one piece with the elongated member. This can be achieved by providing the elongated member in the form of a wire.

According to some embodiments, the second handling portion is formed of an end of the elongated member distal to the movement restriction device. The second handling portion can be provided by looping the elongated member at an end thereof. In examples where the elongated member is a wire, the wire can be looped to form the second handling portion. Parts of the loop can then be positioned in the at least one groove or recess on the first handling portion. The loop allows a user of the instrument to easily grasp the second handling portion.

According to some embodiments, the holding device is formed of an end of the elongated member proximal to the movement restriction device. In examples where the elongated member is a wire, an end of the wire may be the holding device. A recess in the movement restriction device may be dimensioned such that the end of the wire can engage the recess.

In some embodiments at least part of the second handling portion has a curved shape.

The disclosed elements of a surgical instrument for placement of a movement restriction device for use in a surgical procedure for treating reflux disease in a patient, may be used for other applications where implants or surgical tools needs to be held and released inside of the body of the patient. A general instrument may comprise a sleeve, a holding device configured to engage a medical implant or surgical tool, wherein the holding device is configured to be placed within the sleeve and be displaceable in relation to the sleeve, a first handling portion connected to the sleeve, and a second handling portion connected to the holding device. The handling of at least one of the first and second handling portion creates relative displacement of the holding device in relation to the sleeve, which disengages the holding device from the medical implant or surgical tool for performing the placement of the medical implant or surgical tool.

A surgical method for treating reflux disease in a patient by implanting a movement restriction device with use of a surgical instrument is further provided. The surgical method comprises making at least one incision in an abdomen of the patient, dissecting in an area comprising a fundus of a stomach, at least partially inserting the surgical instrument holding the movement restriction device in the abdomen of the patient, placing the movement restriction device contacting the fundus of the stomach, on the outside thereof, fixating the movement restriction device to the fundus wall, and disengaging the movement restriction device by displacing the sleeve in relation to the holding device.

According to one embodiment, the step of fixating the movement restriction device comprises invaginating the movement restriction device in the stomach fundus wall using stomach to stomach sutures or staplers.

According to one embodiment, the surgical method further comprises the step of fixating the stomach to the esophagus using suture of staplers.

In embodiments where the distal portion of the surgical instrument is bent, the surgical procedure may comprise the step of rotating the instrument with the bend for positioning the movement restriction device.

In embodiments where the distal portion of the surgical instrument is operably flexible, the surgical procedure may comprise the step of operating the operably flexible distal portion for positioning the movement restriction device.

According to one embodiment, the holding device comprises a protruding member and the movement restriction device comprises a recess configured to engage the protruding member, and the step of disengaging the movement restriction device by displacing the sleeve in relation to the holding device comprises disengaging the protruding member from the recess.

The surgical method may be a laparoscopic surgical method, in which case the method may further comprise at least one of the steps of:
introducing a tube through the abdominal wall,
filling a fluid or gas into the abdominal cavity,
introducing two or more trocars into the abdominal cavity,
introducing a camera into the abdominal cavity through one of the trocars,
dissecting in the abdomen using a laparoscopic dissection instrument,
introducing the surgical instrument into the abdominal cavity through a trocar,
suturing or stapling using a laparoscopic suturing or stapling instrument, and
removing the surgical instrument into the abdominal cavity through a trocar.

Please note that any embodiment or part of embodiment as well as any method or part of method or any apparatus or part of apparatus or any feature or part of feature or any system or part of system or any figure or part of figure could be combined in any applicable way. All examples herein should be seen as part of the general description and therefore possible to combine in any way in general terms.

BRIEF DESCRIPTION OF DRAWINGS

The invention is now described, by way of example, with reference to the accompanying drawings, in which:

FIG. 4 shows the surgical instrument, according to a first embodiment, in its straight state, in section.

FIG. 5 shows the surgical instrument, according to a first embodiment, in its bent state, in section.

FIG. 6A shows the surgical instrument, according to a first embodiment, when disengaging the movement restriction device, in section.

FIG. 6B shows the surgical instrument, according to an alternative first embodiment, when disengaging the movement restriction device, in section.

FIG. 7A shows the surgical instrument, according to a second embodiment, when disengaging the movement restriction device, in section.

FIG. 7B shows the surgical instrument, according to a second embodiment, when disengaging the movement restriction device, in section.

FIG. 10 shows the medical instrument according to a third embodiment.

DETAILED DESCRIPTION

Figure 1:
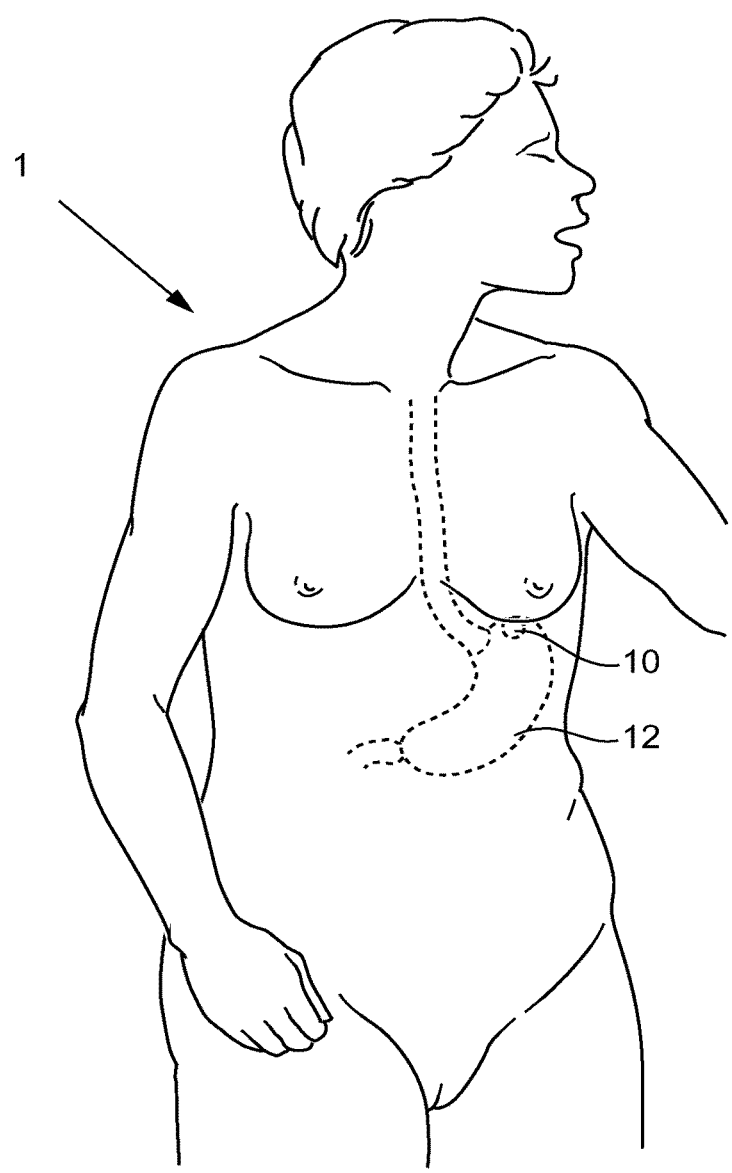
FIG. 1 shows a patient when a movement restriction device has been implanted.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, it should further be noted that features in the different embodiments having different first digit but the same last two digits are similar i.e. 110, 210 and 310. A feature in one embodiment could thus be exchanged for a feature from another embodiment having the same last two digits unless clearly contradictory. The descriptions of the similar features having the same last two digits should thus be seen as complementing each other in describing the fundamental idea of the feature and thereby showing the features versatility.

The terms cardia sphincter, cardia muscle and lower esophageal sphincter is to be understood as the sphincter in the esophagus hindering stomach content and stomach acid from reaching the esophagus.

Surgical procedure is to be understood as any type of surgical procedure, open surgical procedure or laparoscopic surgical procedure. In all of the embodiments herein the surgical instrument may be configured to be inserted into the abdomen of a patient through a laparoscopic trocar. The surgical instrument may in such cases be configured for insertion into a laparoscopic trocar having a diameter of 80 mm, 100 mm, 120 mm or 150 mm.

FIG. 1 shows a human patent 1 when a surgical procedure for the treatment of reflux disease has been performed. A movement restriction device 10 has been placed in the fundus portion of the stomach 12. The function and the operation of the movement restriction device 10 will be described and explained in detail in the following description.

Figure 2:
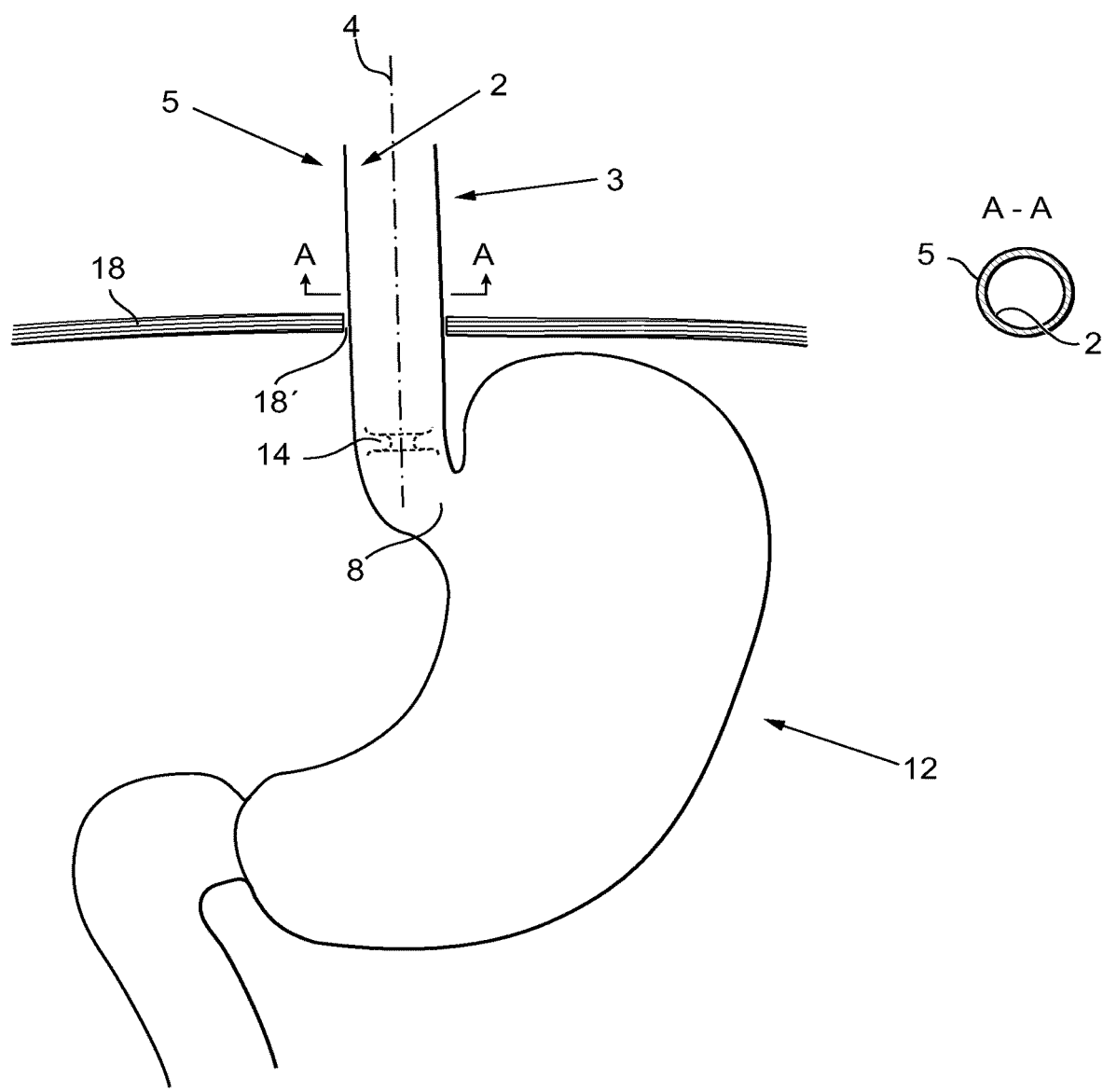
FIG. 2 shows an anatomic view of the stomach, lower portion of the esophagus and the diaphragm.

FIG. 2 shows the stomach region of a patient comprising the esophagus 5 which passes through the thoracic diaphragm 18 which further supports the cardia sphincter 14, which in turn prevents the stomach content and stomach acid from reaching the area of the esophagus 5. The esophagus 5 is a substantially tube shaped tissue leading to the stomach 12 comprising stomach tissue. The esophagus has an esophagus center axis 4, being substantially aligned with a cranial-caudal axis of the patient in and having a substantially circular circumference substantially aligned with a horizontal plane of the erect patient. The esophagus 5 further has an inner 2 and outer 3 substantially cylindrical surface extending radially in relation to the esophagus 5 center axis 4.

In a patient with reflux disease, the cardia sphincter 14 has slid up through the foramen 18' in the thoracic diaphragm 18 and thus is no longer supported by the thoracic diaphragm 18. Reflux disease makes the stomach content and stomach acid enter the esophagus 5 and creates a burning sensation in the esophagus tissue, which in long term exposure could affect the cell structure of the inner layer of esophagus tissue transforming the structure from a squamous epithelium to a gland epithelium, a transformation which increases the risk of adenocarcinoma. The esophagus 5 connects to the stomach at the gastroesophageal junction 8 which normally is placed below the thoracic diaphragm 18. In the event that the cardia sphincter slides up through the foramen 18' in the diaphragm 18, the gastroesophageal junction 8 may be positioned in the foramen 18' or in thorax.

Figure 3:
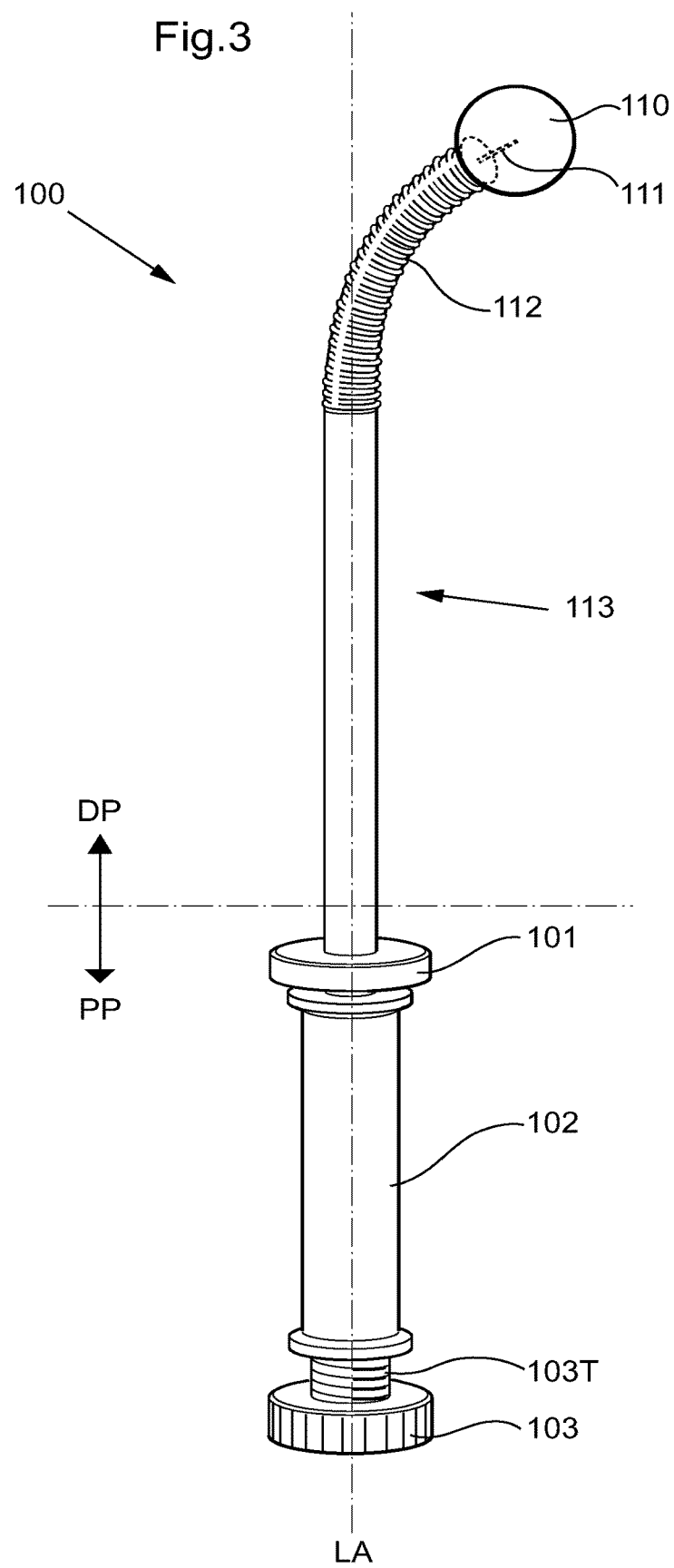
FIG. 3 shows the surgical instrument, according to a first embodiment.

FIG. 3 shows a first embodiment of a surgical instrument 100 for placement of a movement restriction device 110 for use in the surgical procedure for treating reflux disease in a patient. The instrument 100 is made up of a distal portion DP, configured to be inserted into the abdomen of the patient during the surgical procedure, and a proximal portion PP configured to remain outside the body of the patient, and be handled by the surgeon during the surgical procedure. The instrument 100 comprises a sleeve 113, the major part of which being placed at the distal portion DP. The sleeve 113 is connected to or, integrated with, a first handling portion 101, which is displaceable in relation to the second handling portion 102. In the embodiment shown in FIG. 3, a portion of the distal portion is flexible, such that the distal portion can flex and thus bend in relation to a primary length axis LA of the instrument 100. In the embodiment shown in FIG. 3, the flexible portion of the distal portion DP is operably flexible such that the surgeon can bend the distal portion during the surgical procedure. In alternative embodiments, the flexible portion can only be bent manually, outside of the patient and ahead of the surgical procedure, such that a suitable angle of the flexible distal portion can be set for the current patient.

Returning to the embodiment shown in FIG. 3, the distal portion of the sleeve 113 comprises a flexible sleeve portion 112. The flexible sleeve portion 112 could for example comprise a helically wound metal sleeve, a flexible sleeve made from a polymer material, a woven flexible metal sleeve, or a combination of the above.

The distal portion DP of the instrument 100 further comprises a holding device 111 configured to engage and thus hold the movement restriction device 110 during the surgical procedure. The holding device 111 is configured to be placed within the sleeve 113 and be displaceable in relation to the sleeve 113. In the embodiment shown in FIG. 3, the holding device 111 comprises a protruding member configured to engage a recess of the movement restriction device 110, and thereby hold the movement restriction device 110. The movement restriction device is connected to, or integrated with, a third handling portion 103 connected to the holding device 111, which is displaceable in relation to the second handling portion 102 (which will be further elaborated on with reference to FIGS. 4-6).

FIGS. 4 and 5 shows the surgical instrument 100 according to the first embodiment, in section. To start with the most distal part, the movement restriction device 110 is held by the holding device 111 having a protruding member which engages a recess of the movement restriction device 110. The protruding member is fixated to or integrated with the uppermost portion 114' of an elongated member 114. The elongated member 114 is operably flexible such that the surgeon can bend the distal portion DP during the surgical procedure.

The operation device creating the bending motion comprises a plurality of bending elements 116 having a triangular cross-section, such that the bending elements 116 contacts each other on the left side of the elongated member 114 and are separated by a void on the right side of the elongated member 114. A pull wire 115 is fixated to the right side of the uppermost bending element 116 and configured to exert a pulling force on the uppermost bending element, whereby the geometry of the bending elements 116 forces the elongated member 114 to bend and the voids between the bending elements 116 to become smaller. The flexible sleeve portion 112 bends along with the elongated member 114 placed therein. As the sleeve 113 comprises a rigid portion and a flexible sleeve portion 112 configured to bend, and as the sleeve 113 is displaceable relative to the elongated member 114 and the holding device, the point on the surgical instrument in whi3ch the bending may start can be moved by displacing the sleeve 113 which creates a further means for adjusting the instrument.

The proximal portion of the elongated member 114 is connected to, or integrated in, the second handling portion 102, and thus is the uppermost portion 114' of an elongated member 114 and the holding device 111 connected to the second handling portion 102. The pull wire 115 is connected to a third handling portion 103 being the most distal portion of the instrument 100. The third handling portion 103 is rotationally displaceable in relation to the second handling portion 102 around a primary length axis LA of the instrument, for operating the pull wire 115 and thus the operably flexible distal portion during the surgical procedure. The third handling portion 103 comprises a threaded portion 103T and the second handling portion 102 comprises a corresponding threaded portion 102T, such that rotational displacement of the third handling portion 103 in relation to the second handling portion 102 creates linear displacement of the third handling portion 103 in relation to the second handling portion 102, along the primary length axis LA of the instrument 100. The linear displacement pulls the pull wire 115 in the proximal direction causing the operably flexible distal portion to bend.

FIG. 5 shows the first embodiment of the surgical instrument 100 when the third handling portion 103 has been operated by rotation such that the pull wire 115 has been pulled a distance sufficient for the bending elements 116 to bend the operably flexible distal portion to an angle α between the main length axis LA of the instrument and a bend axis BA, being a length axis of the uppermost portion 114' of an elongated member and of the holding device 111.

In one embodiment, the operably flexible distal portion is configured to bend to an angle α exceeding 20°. In one embodiment the operably flexible distal portion is configured to bend to an angle α exceeding 30°. In one embodiment the operably flexible distal portion is configured to bend to an angle α exceeding 45°. In one embodiment the operably flexible distal portion is configured to bend to an angle α exceeding 60°. In one embodiment the operably flexible distal portion is configured to bend to an angle α exceeding 75°. In one embodiment the operably flexible distal portion is configured to bend to an angle α exceeding 90°.

In an alternative embodiment, the third handling portion is a linearly displaceable handling portion directly causing a linear pull on the pull wire 115. I.e. the third handling portion is in such an embodiment slideably connected to the second handling portion and can in such an embodiment be pulled in a proximal direction, along a primary length axis LA of the instrument, for creating the bending of the operably flexible distal portion.

Turning now to the operation of the holding device 111. FIG. 6A shows the surgical instrument 100 in accordance with the first embodiment in its straight configuration, in section. The first handling portion 101 is linearly displaceable in relation to the second handling portion 102 along the primary length axis LA of the instrument. As the first handling portion 101 is integrated with the sleeve 113, linear displacement of the first handling portion 101 in the distal direction causes the distalmost portion of the sleeve 113 to also move in the distal direction and thus be advanced over and passed the uppermost portion 114' of an elongated member 114 and passed the holding device 111. This relative displacement of the sleeve 113 and the holding device 111 disengages the holding device 111 from the movement restriction device 110, by the protruding member of the holding device being disengaged from the recess in the movement restriction device 110. The surgical instrument 100 thus places the movement restriction device inside of the body of the patient and can then be removed from the abdomen.

FIG. 6B shows an alternative embodiment of the surgical instrument 100 in which the first handling portion 101 is rotationally displaceable in relation to the second handling 102 portion around a primary length axis LA of the instrument. The first handling portion 101 comprises a threaded portion 101T and the second handling portion 102 and/or the sleeve 113 comprises a corresponding threaded portion 113T, such that rotational displacement of the first handling portion 101 in relation to the second handling portion 102 creates linear displacement of the first handling portion 101 in relation to the second handling portion 101, along the primary length axis LA of the instrument.

FIGS. 7A and 7B shows a second embodiment of the surgical instrument 200. In the second embodiment, the distal portion DP is bent in relation to the primary length axis LA of the instrument 200 by means of a fixed bend. In the embodiment shown in FIG. 7A the primary length axis LA is bent in relation to a bent axis BA of the holding device 211 and movement restriction device 210 with an angle β. In one embodiment, the angle β of the bend is exceeding 20°. In one embodiment, the angle β of the bend is exceeding 30°. In one embodiment the angle β of the bend is exceeding 45°. In one embodiment the angle β of the bend is exceeding 60°. In one embodiment the angle β of the bend is exceeding 75°. In one embodiment the angle β of the bend is exceeding 90°.

In the embodiment shown in FIG. 7A, the sleeve 213 is rigid and comprises a rigid bend 213B while a distal portion of the elongated member 214 is flexible and creates a flexible bend 214B within the sleeve 213, such that the elongated member 214 can be displaced in relation to the sleeve 213 even though the bend is fixed.

In an alternative embodiment, a distal portion of the elongated member 214 is rigid and comprises a rigid bend, while a distal portion of the sleeve 213 is flexible and forms a flexible bend, such that the elongated member 214 can be displaced in relation to the sleeve 213 even though the bend is fixed.

FIG. 7B shows the second embodiment of the surgical instrument 200 in the state when the elongated member 214 and thus the holding device 211 has been displaced in relation to the sleeve 213, such that the movement restriction device 210 has been disengaged from the instrument.

The instrument according to the second embodiment is shown with the sleeve 213 being directly linearly displaceable in relation to the elongated member 214, however, it is equally conceivable that the instrument according to the second embodiment is equipped with the rotating first handling portion such as shown in FIG. 6B.

FIGS. 8A-8D shows a surgical method for treating reflux disease in a patient by implanting a movement restriction device 310 with use of the surgical instrument 300 according to one of the embodiments herein.

Figure 8A:
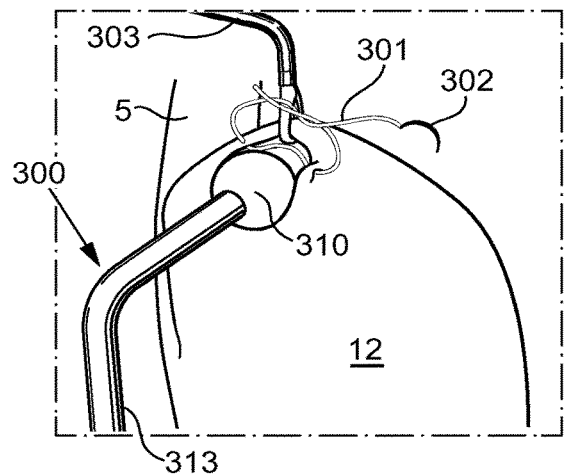
FIGS. 8A-8D shows steps of a surgical procedure for treating reflux disease, using the surgical instrument.

In FIG. 8A, the instrument 300 holding the movement restriction device 310 has been inserted into the abdomen of the patient though an incision made in the abdomen of the patient. The procedural step shown in FIG. 8A has been preceded by the step of dissecting in an area comprising a fundus of a stomach, such that the movement restriction device 310 can be placed engaging the fundus of the patient. A grasper is used for holding the stomach wall of the fundus while the surgical instrument operates to place the movement restriction device contacting the fundus of the stomach, on the outside thereof. In the embodiment when the surgical instrument is bent, the instrument may be positioned by the step of rotating the instrument with the bend for positioning the movement restriction device. In the embodiments where the distal portion of the surgical instrument is operably flexible, the instrument may be positioned by the step of operating the operably flexible distal portion for positioning the movement restriction device.

The disclosed elements of a surgical instrument for placement of a movement restriction device for use in a surgical procedure for treating reflux disease in a patient, may be used for other applications where implants or surgical tools needs to be held and released inside of the body of the patient. A general instrument may comprise a sleeve, a holding device configured to engage a medical implant or surgical tool, wherein the holding device is configured to be placed within the sleeve and be displaceable in relation to the sleeve, a first handling portion connected to the sleeve, and a second handling portion connected to the holding device. The handling of at least one of the first and second handling portion creates relative displacement of the holding device in relation to the sleeve, which disengages the holding device from the medical implant or surgical tool for performing the placement of the medical implant or surgical tool.

In the surgical procedure shown in FIGS. 8A-8D, the movement restriction device is invaginated in the stomach fundus wall by means of stomach to stomach sutures 301 by means of a surgical suturing needle. It is however equally conceivable that a stapling device is used in the step of invaginating the movement restriction device in the stomach wall.

Figure 8B:
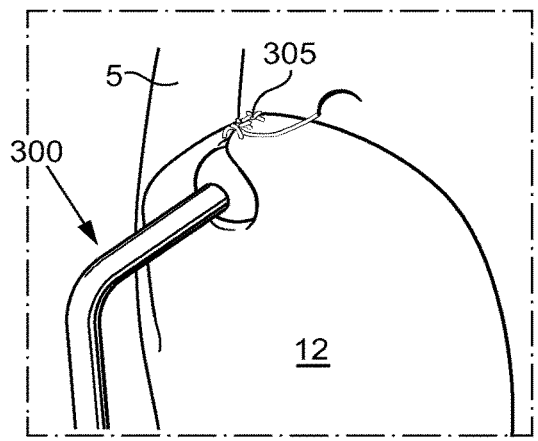
Figure 8C:
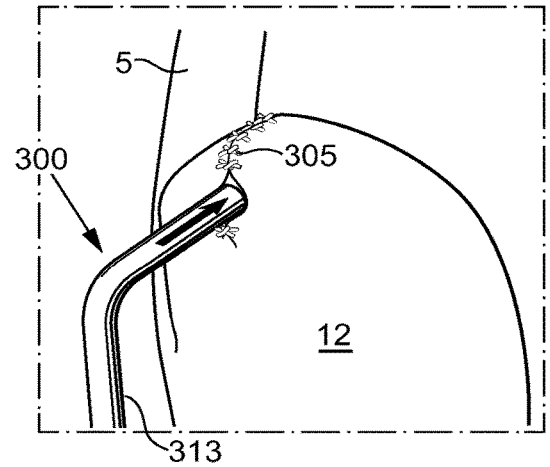

FIGS. 8B and 8C shows the further suturing for invaginating the movement restriction device 310, such that the movement restriction device 310 is placed fixedly in the created pouch on the outside of the stomach wall, on the outside thereof.

Figure 8D:
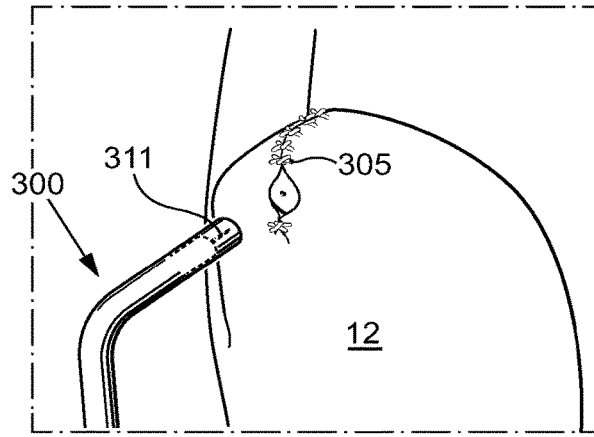

FIG. 8D shows the step of the instrument disengaging the movement restriction device by displacing the sleeve 313 in relation to the holding device 311. In the embodiment shown in FIGS. 8A-8D, the holding device 311 comprises a protruding member and the movement restriction device 310 comprises a recess configured to engage the protruding member, such that the step of disengaging the movement restriction device 310 by displacing the sleeve 313 in relation to the holding device 311 comprises disengaging the protruding member from the recess. Subsequently the instrument 310 is removed from the abdomen of the patient.

The procedural steps shown on FIGS. 8A-8D may be steps of a laparoscopic surgical method, in which case the surgical method further comprises the steps of introducing a tube through the abdominal wall for filling a fluid or gas into the abdominal cavity, to thereby expand the abdominal cavity creating visual space. The method further comprises introducing two or more trocars into the abdominal cavity and introducing a camera into the abdominal cavity through one of the trocars. Next, the method comprises dissecting in the abdomen using a laparoscopic dissection instrument, before the introduction of the surgical instrument into the abdominal cavity through a trocar. The fixation by means of sutures or staplers is performed using a laparoscopic suturing or stapling instrument, and the method is concluded by the removal of the surgical instrument into the abdominal cavity through a trocar.

Figure 9:
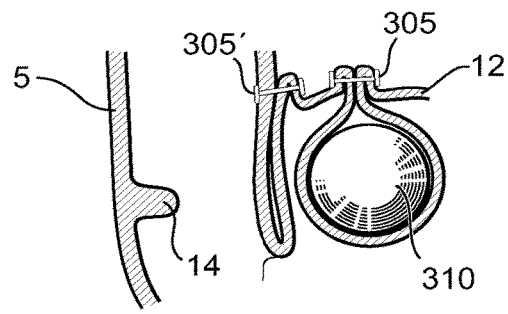
FIG. 9 shows the esophagus and upper part of the stomach when the movement restriction device has been positioned, in section.

FIG. 9 shows the esophagus and the upper portion of the stomach when the movement restriction device has been implanted in the fundus wall. The movement restriction device is fixated by invagination in the stomach 12 wall by means of a plurality of sutures 305. In the embodiment shown in FIG. 9, the fixation of the movement restriction device has been preceded by the fixation of the stomach fundus wall to the esophagus by means of sutures 305' for the fixed placement of the movement restriction device 310. The movement restriction device 310 is preferably made from an elastic, bio-compatible silicone material which may be provided with at least one layer. For example, a metal layer, a Parylene layer, a polytetrafluoroethylene layer or a polyurethane layer.

The movement restriction device may have a maximum diameter of less than 40 mm, or a maximum diameter of less than 30 mm, or a maximum diameter of less than 20 mm.

FIG. 10 shows a third embodiment of a surgical instrument 100 for placement of a movement restriction device 110 for use in the surgical procedure for treating reflux disease in a patient. As shown in FIGS. 10-12B, the movement restriction device 110 has a body having a substantially spherical shape comprising a plurality of facets. As shown in FIGS. 10-12B, the body has two facets arranged orthogonally with respect to one another, or more specifically the body has three facets arranged orthogonally with respect to one another. In other terms, the movement restriction device 110 shown in FIGS. 10-12B has a body having a substantially cubical shape with rounded edges and corners. The instrument shown in the third embodiment is similar to the instrument shown in the first embodiment and the corresponding elements are numbered alike. The instrument 100 comprises a sleeve 113. The sleeve 113 is connected to, or integrated with, a first handling portion 101. The first handling 101 portion comprises a proximal part P and distal part D. The first handling portion 101 preferably comprises grooves or recesses in which parts of a second handling portion 102 can be positioned. The second handling portion 102 is preferably integrated with an elongated member 114 extending along the longitudinal axis inside the sleeve 113. The second handling portion 102 may be formed by forming a loop of the proximal end of the elongated member such that it can be held in place in the first handling portion 101 by the grooves or recesses thereof. The elongated member may preferably be a wire. The first handling portion 101 may further comprise at least one stopping portion 104a, 104b adapted to stop the relative displacement of the second handling portion 102 at a predetermined amount of displacement.

The instrument 100 further comprises a holding device 111 configured to engage and thus hold the movement restriction device 110 during the surgical procedure. The holding device 111 is configured to be placed within the sleeve 113 and be displaceable in relation to the sleeve 113. The holding device 111 may be integrated with the elongated member 114 such that relative displacement between the first handling portion 101 and the second handling portion 102 leads to relative displacement between the sleeve 113 and the holding device 111. In the embodiment shown in FIG. 10, the holding device 111 comprises a protruding member configured to engage a recess of the movement restriction device 110, and thereby hold the movement restriction device 110.

Figure 11A:
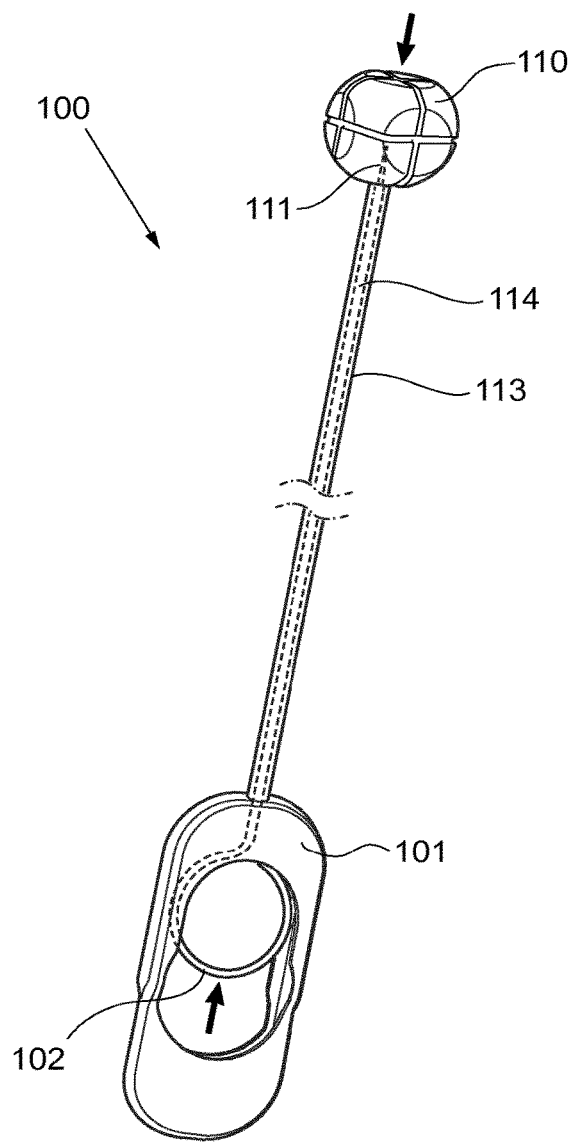
FIG. 11A shows the surgical instrument, according to a third embodiment, when engaging the movement restriction device.
Figure 11B:
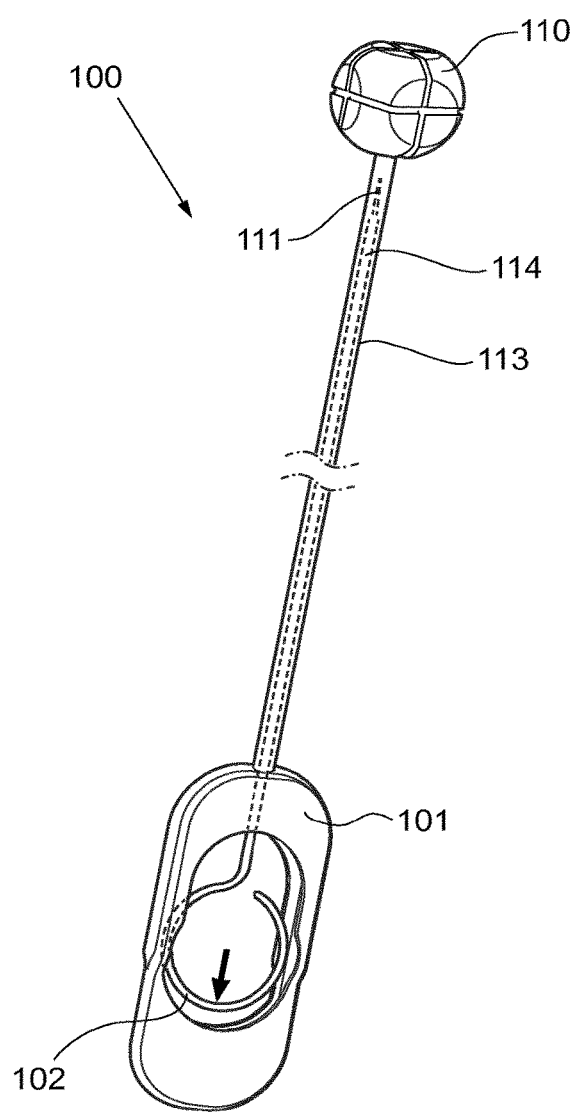
FIG. 11B shows the surgical instrument, according to a third embodiment, when disengaging the movement restriction device.

Turning now to the operation of the holding device 111. FIGS. 11A and 11B show the surgical instrument 100 in accordance with the third embodiment. In FIG. 11A, the second handling portion 102 formed as a looped proximal end of the elongated member 114, and positioned partly within the grooves or recesses of the first handling portion. The proximal end of the elongated member 114 ends in the holding device 111. When the second handling portion 102 is positioned in the proximal position in the first handling portion 101, the holding device 111 extends out of the sleeve 113 such that that the holding member 111 can engage the movement restriction device 110.

The first handling portion 101 is linearly displaceable in relation to the second handling portion 102 along the primary length axis of the instrument. As the first handling portion 101 is integrated with the sleeve 113, linear displacement of the first handling portion 101 in the distal direction causes the distalmost portion of the sleeve 113 to also move in the distal direction and thus be advanced over and passed the uppermost portion of an elongated member 114 and passed the holding device 111. This relative displacement of the sleeve 113 and the holding device 111 disengages the holding device 111 from the movement restriction device 110, by the protruding member of the holding device 111 being disengaged from the recess in the movement restriction device 110. In practice, as shown in FIG. 11B this relative displacement can be achieved by handling the second handling portion 102 from the distal position in the first handling portion 101 to the proximal position in the first handling portion. This achieves a relative displacement of the sleeve 113 and the holding device 111 which disengages the holding device 111 from the movement restriction device 110. The surgical instrument 100 thus places the movement restriction device inside of the body of the patient and can then be removed from the abdomen.

Figure 12A:
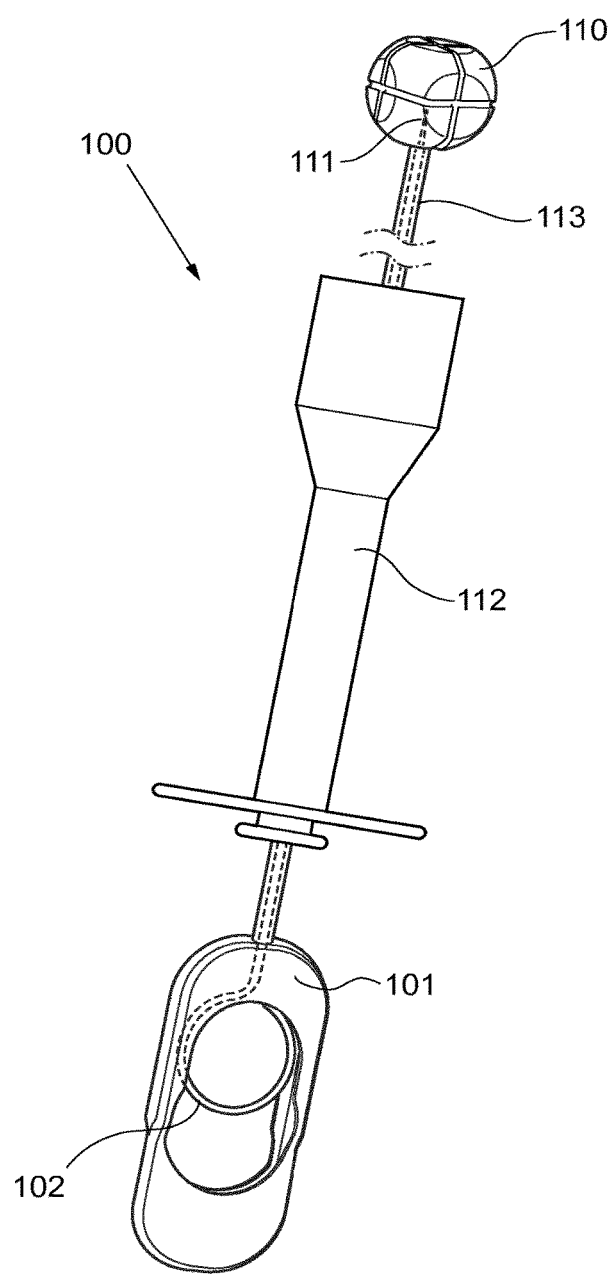
FIG. 12A shows the surgical instrument, according to a third embodiment when positioned inside a trocar, engaging the movement restriction device.
Figure 12B:
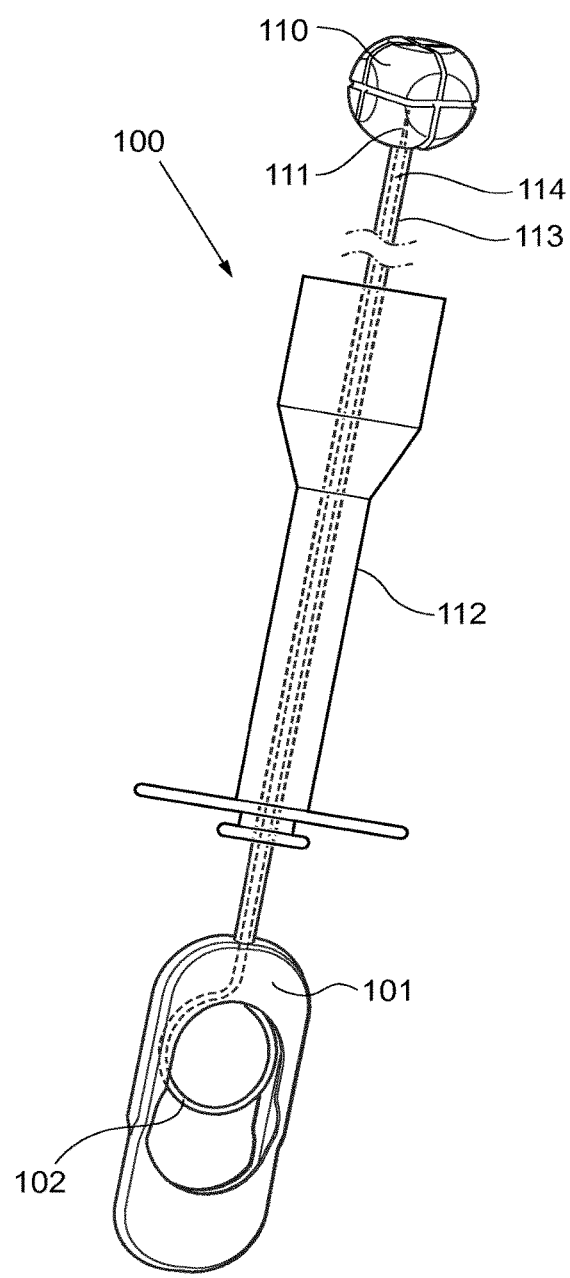
FIG. 12B shows the surgical instrument, according to a third embodiment when positioned inside a trocar, engaging the movement restriction device.

FIGS. 12A and 12B show the surgical instrument 100 according to the third embodiment, when positioned inside a trocar 112 in a side view. The trocar 112 assists in expanding the abdominal wall tissue such that the movement restriction device 110 can be positioned in the stomach wall. When the surgical instrument 100 has placed the movement restriction device inside the body as described above, the surgical instrument 100 can be removed from the trocar 112 and subsequently the trocar 112 can be removed from the body.

Please note that any embodiment or part of embodiment as well as any method or part of method or any apparatus or part of apparatus or any feature or part of feature or any system or part of system could be combined in any applicable way. All examples herein should be seen as part of the general description and therefore possible to combine in any way in general terms.

The invention claimed is:

1. A movement restriction device for use in a surgical procedure for treating reflux disease in a patient, the movement restriction device being adapted to restrict movement of the cardia sphincter and to contact the fundus of the patient's stomach,
   wherein the movement restriction device has a body having a spherical shape comprising a plurality of facets, and wherein the movement restriction device is adapted to be invaginated by the fundus of the patient's stomach.

2. The movement restriction device according to claim 1, wherein the movement restriction device is further adapted to be completely invaginated by the fundus of the patient's stomach.

3. The movement restriction device according to claim 1, wherein the body has a maximum diameter of less than 20 mm.

4. The movement restriction device according to claim 1, wherein the body has a maximum diameter of less than 30 mm.

5. The movement restriction device according to claim 1, wherein the body has a maximum diameter of less than 40 mm.

6. The movement restriction device according to claim 1, wherein the movement restriction device is made from a biocompatible silicone material.

7. The movement restriction device according to claim 6, wherein the biocompatible silicone material is provided with at least one of a metal layer, a Parylene layer, a polytetrafluoroethylene layer and a polyurethane layer.

8. The movement restriction device according to claim 1, wherein the body has two facets arranged orthogonally with respect to one another.

9. The movement restriction device according to claim 1, wherein the body has three facets arranged orthogonally with respect to one another.

10. A movement restriction device for use in a surgical procedure for treating reflux disease in a patient, the movement restriction device being adapted to restrict movement of the cardia sphincter and to contact the fundus of the patient's stomach,
    wherein the movement restriction device has a body having a cubical shape with rounded edges and corners, and wherein the movement restriction device is adapted to be invaginated by the fundus of the patient's stomach.

11. The movement restriction device according to claim 10, wherein the movement restriction device is further adapted to be completely invaginated by the fundus of the patient's stomach.

12. The movement restriction device according to claim 10, wherein the body has a maximum diameter of less than 20 mm.

13. The movement restriction device according to claim 10, wherein the body has a maximum diameter of less than 30 mm.

14. The movement restriction device according to claim 10, wherein the body has a maximum diameter of less than 40 mm.

15. The movement restriction device according to claim 10, wherein the movement restriction device is made from a biocompatible silicone material.

16. The movement restriction device according to claim 15, wherein the biocompatible silicone material is provided with at least one of a metal layer, a Parylene layer, a polytetrafluoroethylene layer and a polyurethane layer.

* * * * *